United States Patent
Roh et al.

(10) Patent No.: US 11,242,442 B2
(45) Date of Patent: Feb. 8, 2022

(54) ADDITIVE COMPOSITION AND METHOD OF PREPARING THE SAME

(71) Applicant: Korea Kumho Petrochemical Co., Ltd., Seoul (KR)

(72) Inventors: Kee Yoon Roh, Daejeon (KR); Jung Hee Jang, Daejeon (KR); Yun Cheol Park, Asan-si (KR); Nam Hyun Cho, Daejeon (KR)

(73) Assignee: Korea Kumho Petrochemical Co., Ltd., Seoul (KR)

(*) Notice: Subject to any disclaimer, the term of this patent is extended or adjusted under 35 U.S.C. 154(b) by 161 days.

(21) Appl. No.: 16/601,856

(22) Filed: Oct. 15, 2019

(65) Prior Publication Data

US 2020/0115525 A1  Apr. 16, 2020

(30) Foreign Application Priority Data

Oct. 15, 2018 (KR) .......................... 10-2018-0122494

(51) Int. Cl.
*C08K 5/13* (2006.01)
*C08K 5/01* (2006.01)
*C09D 163/00* (2006.01)

(52) U.S. Cl.
CPC .................. *C08K 5/13* (2013.01); *C08K 5/01* (2013.01); *C09D 163/00* (2013.01)

(58) Field of Classification Search
CPC ......................... C09D 163/00–10; C08K 5/13
See application file for complete search history.

(56) References Cited

U.S. PATENT DOCUMENTS

| | | | | |
|---|---|---|---|---|
| 4,906,791 A | * | 3/1990 | Imanari | ................... C07C 37/14 568/744 |
| 2016/0207859 A1 | | 7/2016 | Roh et al. | |
| 2017/0096578 A1 | * | 4/2017 | Roh | ..................... C09D 163/00 |

FOREIGN PATENT DOCUMENTS

| | | |
|---|---|---|
| EP | 3153537 A1 | 4/2017 |
| KR | 10-2017-0021439 A | 2/2017 |
| KR | 2017-0062219 A | 6/2017 |
| KR | 10-1877491 B1 | 7/2018 |

OTHER PUBLICATIONS

Partial machine translation of KR 20170062219 A.*

* cited by examiner

*Primary Examiner* — Kregg T Brooks
(74) *Attorney, Agent, or Firm* — Novick, Kim & Lee, PLLC; Jae Youn Kim

(57) ABSTRACT

An additive composition includes a specific amount of α-methylstyrenated phenol, can be mixed with a main material part or curing agent part for paint, and can suppress the occurrence of a discoloration issue.

12 Claims, 3 Drawing Sheets

(a) In presence of first acid catalyst, reacting phenol-based compound and heat-resistant styrene-based compound (b) In presence of second catalyst, further reacting the product of step (a) with styrene compound (a) In presence of first acid catalyst, reacting phenol-based compound and heat-resistant styrene-based compound (b) In presence of second catalyst, further reacting the product of step (a) with styrene compound

ADDITIVE COMPOSITION AND METHOD OF PREPARING THE SAME

CROSS-REFERENCE TO RELATED APPLICATION

This application claims priority to and the benefit of Korean Patent Application No. 10-2018-0122494, filed on Oct. 15, 2018, the disclosure of which is incorporated herein by reference in its entirety.

BACKGROUND

1. Field of the Invention

The present invention relates to an additive composition and a method of preparing the same, and more specifically, to an additive composition including α-methylstyrenated phenol that may be used as a plasticizer or non-reactive thinner for epoxy paint and a method of preparing the same.

2. Discussion of Related Art

Conventionally, various non-reactive thinners have been used to impart plasticity to epoxy paint and serve as a thinner. Representative examples of the non-reactive thinner include alkylphenols such as nonylphenols, dodecylphenols, octylphenols, and the like, benzyl alcohol, $C_5$-$C_9$ hydrocarbon resins, phenol and styrenated phenol, a mixture of α-methylstyrene oligomers, and the like.

Among those listed above, alkylphenols have been widely used as an additive or surfactant for epoxy paint which requires plasticity in terms of molecular structural and chemical properties. However, since these alkylphenols are known as a substance that causes nephrotoxicity and disrupts the endocrine system, the use thereof is currently being prohibited around the world, or the range of application thereof has been gradually limited.

In addition, when mixed with any curing agent for paint (e.g., polyamide curing agent, Jeffamine D-230), a nonylphenol, a dodecylphenol, and styrenated phenol cause the curing agent to turn red, which makes it difficult to use them as a plasticizer or non-reactive thinner for varnish.

In order to solve these problems, α-methylstyrenated phenol which is a mixture produced by reacting phenol and α-methylstyrene in the presence of an acid catalyst was conventionally used as a non-reactive thinner. However, it was difficult to use the α-methylstyrenated phenol as a plasticizer or non-reactive thinner for paint because an α-methylstyrenated compound is solidified according to a composition ratio of the resulting mixture (Comparative Example 1), or poor compatibility is caused in paint mixing due to the low OH value caused by a difference in the composition ratio.

Accordingly, an additive composition which can be mixed with both a main material part (epoxy resin part) and curing agent part for paint while maintaining a drying time or compatibility at the level of a conventional case where a nonylphenol or a dodecylphenol is used and allows a discoloration issue not to occur or be considerably delayed was prepared in the present invention.

SUMMARY OF THE INVENTION

The present invention has been designed to solve the above-described problems of the prior art, and is directed to providing an additive composition which can be mixed with both a main material part (epoxy resin part) and curing agent part for paint while maintaining a drying time or compatibility at the level of a conventional thinner including a nonylphenol or a dodecylphenol and suppresses a discoloration issue when mixing with a curing agent for paint, and a method of preparing the same.

In one aspect of the present invention, there is provided an additive composition which includes: a first compound, which is produced by reacting a phenol-based compound and a heat-resistant styrene-based compound, at 40 to 100 parts by weight; a second compound, which is produced by reacting a phenol-based compound and a styrene compound, at 2 to 10 parts by weight; a third compound, which is produced by reacting a phenol-based compound, a heat-resistant styrene-based compound, and a styrene compound, at 2 to 20 parts by weight; and a mixture of trimethyl phenyl indane and diphenyl methyl pentene at 2 to 10 parts by weight.

According to one exemplary embodiment, the first compound may include a compound in which a reaction ratio of the phenol-based compound and the heat-resistant styrene-based compound is 1:1 and a compound in which the reaction ratio thereof is 1:2 in a weight ratio of 1:2 to 4.

According to one exemplary embodiment, when a mixture of the additive composition and an amine-based compound is stored under a condition of 50° C., a Gardner color variation may be 0.5 G/week or less.

In another aspect of the present invention, there is provided an epoxy paint composition which includes: an epoxy resin or an epoxy curing agent; and the above-described additive composition.

According to one exemplary embodiment, the epoxy paint composition may have a pot life of 30 minutes or more.

In still another aspect of the present invention, there is provided a method of preparing an additive composition which includes the steps of: (a) preparing a first product by reacting, in the presence of a first acid catalyst, a phenol-based compound and a heat-resistant styrene-based compound; and (b) preparing a second product by further reacting, in the presence of a second acid catalyst, the first product with 0.3 to 1 equivalent of a styrene compound based on 1 equivalent of the phenol-based compound.

According to one exemplary embodiment, the first acid catalyst and the second acid catalyst may each be one selected from the group consisting of sulfuric acid, p-toluenesulfonic acid, methanesulfonic acid, phosphoric acid, a boron trifluoride complex, clay, an ion exchange resin, and a mixture of two or more thereof.

According to one exemplary embodiment, the first acid catalyst and the second acid catalyst may be the same or different.

According to one exemplary embodiment, an equivalent ratio of the phenol-based compound and the first acid catalyst may be 1:0.0001 to 1.

According to one exemplary embodiment, the heat-resistant styrene-based compound may be one selected from the group consisting of α-methylstyrene, α-ethylstyrene, methyl-α-methylstyrene, and a mixture of two or more thereof.

According to one exemplary embodiment, the heat-resistant styrene-based compound may be reacted in an amount of 0.1 to 3 equivalents based on 1 equivalent of the phenol-based compound.

According to one exemplary embodiment, the first product may include: a mixture of trimethyl phenyl indane and diphenyl methyl pentene at 1 to 10 wt %; cumylphenol at 30 to 70 wt %; dicumylphenol at 10 to 40 wt %; and phenol as the remainder.

According to one exemplary embodiment, the second product may include: a mixture of trimethyl phenyl indane and diphenyl methyl pentene at 2 to 10 wt %; cumylphenol at 10 to 50 wt %; dicumylphenol at 30 to 50 wt %; styrenated phenol at 2 to 10 wt %; and α-methylstyrenated phenol, to which styrene has been bonded, at 2 to 20 wt %.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
FIG. 1 is a schematic diagram of a method of preparing an additive composition according to the example of the present invention.

Hereinafter, exemplary embodiments of the present invention will be described in detail with reference to accompanying drawings. However, it should be understood that the present invention can be implemented in various forms, and that it is not intended to limit the present invention to the exemplary embodiments. Also, in the drawings, descriptions of parts unrelated to the detailed description are omitted to clearly describe the present invention. Throughout the specification, like numbers refer to like elements.

Throughout this specification, when a part is mentioned as being "connected" to another part, this means that the part may not only be "directly connected" to the other part but may also be "indirectly connected" to the other part through another member interposed therebetween. In addition, when a part is mentioned as "including" a specific component, this does not preclude the possibility of the presence of other component(s) in the part which means that the part may further include the other component(s), unless otherwise stated.

When a numerical value is presented herein, the value has the precision of the significant digit provided in accordance with the standard rules in chemistry for significant digits unless its specific range is stated otherwise. For example, the numerical value 10 includes the range of 5.0 to 14.9 and the numerical value 10.0 includes the range of 9.50 to 10.49.

As used herein, the term "equivalent" refers to a value obtained by dividing the weight of a reactant or a catalyst by its molecular weight.

Hereinafter, exemplary embodiments of the present invention will be described in more detail with reference to the accompanying drawings.

Additive Composition

An additive composition according to one aspect of the present invention includes: a first compound, which is produced by reacting a phenol-based compound and a heat-resistant styrene-based compound, at 40 to 100 parts by weight; a second compound, which is produced by reacting a phenol-based compound and a styrene compound, at 2 to 10 parts by weight; a third compound, which is produced by reacting a phenol-based compound, a heat-resistant styrene-based compound, and a styrene compound, at 2 to 20 parts by weight; and a mixture of trimethyl phenyl indane and diphenyl methyl pentene at 2 to 10 parts by weight.

The first compound may include a compound in which a reaction ratio of the phenol-based compound and the heat-resistant styrene-based compound is 1:1 and a compound in which the reaction ratio thereof is 1:2 in a weight ratio of 1:2 to 4, preferably, in a weight ratio of 1:3.

The first compound, second compound, and third compound may, for example, have structures represented by the following Chemical Formulas 1, 2, and 3 respectively. For example, the first compound may be α-methylstyrenated phenol, and the second compound may be styrenated phenol.

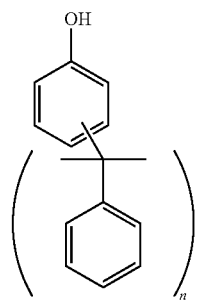

[Chemical Formula 1]

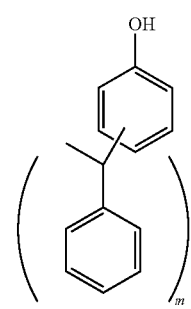

[Chemical Formula 2]

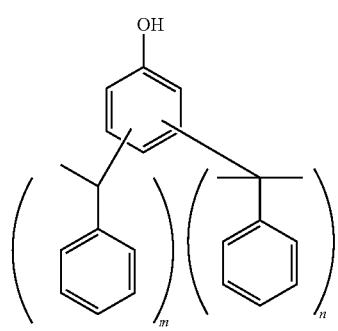

[Chemical Formula 3]

In Chemical Formulas 1, 2, and 3, n is an integer of 1 or 2, and m is an integer of 1 or 2.

The additive composition may have an OH value of 150 to 250, 175 to 225, or 180 to 195. When the OH value of the additive composition is less than 150, a drying time (compatibility) is poor, or physical properties are degraded, and thus the use of the additive composition as a thinner may be limited.

The additive composition may be a liquid. If the additive composition is a crystalline solid, the use of the additive composition as a thinner may be limited.

"Gardner color" is a standard for measuring the color tone of a resin or transparent liquid such as fatty oil or the like, and is an index that can estimate contamination, impurities, degradation of products, and the like through a change in color. A Gardner index that represents the Gardner color may be analyzed by visual comparison with the Gardner color scale, a spectrophotometer, or the like.

When mixed with an amine-based compound, common additives such as a thinner and the like including phenol derivatives react to cause structural modifications, and thus red or yellow discoloration results. This discoloration makes it difficult to use the thinner as an additive for varnish.

When a mixture of the additive composition and the amine-based compound is stored under a condition of 50° C., a Gardner color variation may be 0.5 G/week or less. The amine-based compound may be, for example, a curing agent of an epoxy resin such as the polyetheramine Jeffamine D-230 or the like. The mixture may be prepared by mixing the additive composition and the amine-based compound in a weight ratio of 1:1.

After being mixed with an amine-based compound and then stored at 50° C. for 2 weeks, a conventional additive composition including a nonylphenol or a dodecylphenol exhibits a Gardner index increased about 3 fold compared to the initial color, whereas the additive composition of the present invention can exhibit the change in Gardner index decreased to less than 15% under the same conditions.

Epoxy Paint Composition

An epoxy paint composition according to another aspect of the present invention includes an epoxy resin or an epoxy curing agent; and the above-described additive composition. The epoxy paint composition may further include various materials, as necessary, in addition to the epoxy resin, the epoxy curing agent, or the additive composition.

In two-component epoxy paint, a portion including the epoxy resin is referred to as a main material part (epoxy resin part), and a portion including the epoxy curing agent is referred to as a curing agent part (epoxy curing part). The two-component epoxy paint may be prepared by mixing the main material part and the curing agent part and then cured. The additive composition may be mixed with the main material part, the curing agent part, or both of them.

When applied into a thickness of 400 μm, the epoxy paint may be dried to touch within 7.5 hours, and may be dried hard within 12.5 hours. These are the similar levels to those of a nonylphenol used as a conventional thinner for epoxy paint, and may be faster than a dodecylphenol.

The "pot life" means the time in which the epoxy paint composition may be used as paint from the mixing point of time, and is defined as the amount of time it takes for an initial mixed viscosity to double in accordance with ASTM D-2471.

The epoxy paint composition may have a pot life of 30 minutes or more. If the pot life is too long or short, practical application of the epoxy paint composition is difficult. The epoxy paint composition may have a pot life of 60 minutes or less, 50 minutes or less, or 40 minutes or less, but the present invention is not limited thereto.

The epoxy paint composition including the additive composition may exhibit harmoniously enhanced abrasion resistance, weather resistance, adhesion, and storability compared to a conventional case including a thinner using a nonylphenol or a dodecylphenol. This may not only result from α-methylenestyrenated phenol being included in the additive composition, but because each compound is harmoniously composed.

Method of Preparing Additive Composition

FIG. 1 is a schematic diagram of a method of preparing an additive composition of the present invention.

Referring to FIG. 1, a method of preparing an additive composition according to still another aspect of the present invention includes the steps of: (a) preparing a first product by reacting, in the presence of a first acid catalyst, a phenol-based compound and a heat-resistant styrene-based compound; and (b) preparing a second product by reacting, in the presence of a second acid catalyst, the first product with 0.3 to 1 equivalent of a styrene compound based on 1 equivalent of the phenol-based compound.

An example of the reactions in the steps (a) and (b) may be represented by the following Reaction Scheme 1.

[Reaction Scheme 1]

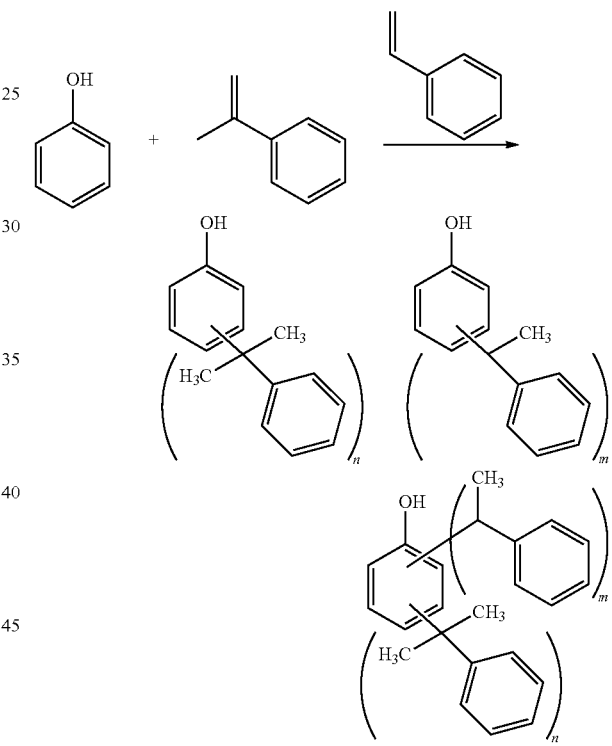

In Reaction Scheme 1, n is an integer of 1 or 2, and m is an integer of 1 or 2.

Referring to Reaction Scheme 1, phenol and α-methylstyrene may react in the presence of an acid catalyst to produce α-methylstyrenated phenol. According to the reaction, cumylphenol in which one molecule of phenol and one molecule of α-methylstyrene are bonded, dicumylphenol in which one molecule of phenol and two molecules of α-methylstyrene are bonded, styrenated phenol in which one molecule of phenol and one or two molecules of styrene are bonded, and α-methylstyrenated phenol to which styrene has been bonded may be produced, and unreacted materials may remain.

The ratio of the products may be adjusted according to an equivalent ratio of the phenol-based compound, the heat-resistant styrene-based compound, and the styrene compound which are reactants, a type and content of the catalyst, a reaction temperature, and a reaction time.

The phenol-based compound may be used alone or in combination of a derivative thereof, and may be one selected from the group consisting of phenol, o-cresol, m-cresol, p-cresol, 2,5-xylenol, 3,5-xylenol, 3,4-xylenol, 2,3-xylenol, o-ethylphenol, m-ethylphenol, p-ethylphenol, p-tert-butylphenol, p-octylphenol, m-methoxyphenol, p-methoxyphenol, 3,4-dimethoxyphenol, 2-methoxy-4-methylphenol, m-ethoxyphenol, p-ethoxyphenol, m-propoxyphenol, p-propoxyphenol, m-butoxyphenol, p-butoxyphenol, 2-methyl-4-isopropylphenol, o-chlorophenol, m-chlorophenol, p-chlorophenol, dihydroxybiphenyl, bisphenol A, phenylphenol, resorcinol, naphthol, and a mixture of two or more thereof, but the present invention is not limited thereto.

The first acid catalyst and the second acid catalyst may each be one selected from the group consisting of sulfuric acid, p-toluenesulfonic acid, methanesulfonic acid, phosphoric acid, a boron trifluoride complex, clay, an ion exchange resin, and a mixture of two or more thereof. Preferably, the first acid catalyst is sulfuric acid or p-toluenesulfonic acid, and the second acid catalyst is sulfuric acid, but the present invention is not limited thereto.

The first acid catalyst and the second acid catalyst may be the same or different. Particularly, when the first acid catalyst and the second acid catalyst are the same, the reaction may be continuously performed without further adding a separate catalyst.

Since the reaction of the step (a) is an exothermic reaction, the temperature increases as the reaction proceeds. Therefore, the step (a) may be performed at 50° C. or more, 55° C. or more, or 60° C. or more, 200° C. or less, 190° C. or less, 180° C. or less, 170° C. or less, 160° C. or less, 150° C. or less, 140° C. or less, 130° C. or less, or 120° C. or less. When the reaction temperature is less than 50° C., the activity of the catalyst is degraded, and thus a reaction rate may decrease, and when the reaction temperature is greater than 200° C., the product may be discolored during the reaction.

The heat-resistant styrene-based compound may be one selected from the group consisting of α-methylstyrene, α-ethylstyrene, methyl α-methylstyrene, and a mixture of two or more thereof, and is preferably α-methylstyrene. However, styrene is not included in the heat-resistant styrene-based compound.

In the step (a), an equivalent ratio of the phenol-based compound and the first acid catalyst may be 1:0.0001 to 1, preferably, 1:0.001 to 1. When the first acid catalyst is reacted in an amount of less than 0.0001 equivalent based on 1 equivalent of the phenol, a reaction rate may be degraded, and when the first acid catalyst is reacted in an amount of greater than 1 equivalent, it may be difficult to adjust the composition of the first product due to excessive reactivity.

In the step (a), for example, cumylphenol may be produced by reacting one molecule of phenol and one molecule of α-methylstyrene, dicumylphenol may be produced by reacting one molecule of phenol and two molecules of α-methylstyrene, an α-methylstyrene dimer (AMS dimer) may be produced by reacting α-methylstyrenes, and unreacted materials remain as the remainder. Therefore, the first product may be present in the form of a mixture thereof.

The cumylphenol may be present in the form of a mixture of o-cumylphenol, m-cumylphenol, and p-cumylphenol in which the α-methylstyrene is bonded at the ortho, meta, and para positions of the phenol respectively, but p-cumylphenol may be predominantly produced due to the steric factors between α-methylstyrene and phenol caused by the hydroxyl group of the phenol which is an electron donating group (EDG).

In addition, the α-methylstyrene dimer (AMS dimer) may be produced by the reaction between two molecules of α-methylstyrene according to a binding site, and may specifically be a mixture of trimethyl phenyl indane (TMPI) and diphenyl methyl pentene (DMP) such as 4-methyl-2,4-diphenyl-1-pentene and 4-methyl-2,4-diphenyl-2-pentene.

Specifically, the first product may include the mixture of TMPI and DMP at 1 to 10 wt %, cumylphenol at 30 to 70 wt %, dicumylphenol at 10 to 40 wt %, and a phenol-based compound as the remainder.

In the step (b), in the presence of a second acid catalyst, the first product may further react with 0.3 to 1 equivalent, preferably, 0.3 to 0.8 equivalent of a styrene compound based on 1 equivalent of the phenol-based compound to prepare a second product.

By further reacting the styrene compound with an unreacted residual phenol-based compound and the first product, the second product may be present in the form of a mixture of cumylphenol, dicumylphenol, an AMS dimer, a styrenated phenol compound, and α-methylstyrenated phenol to which styrene has been bonded.

Since the reaction of the step (b) is also an exothermic reaction, the temperature increases as the reaction proceeds. Therefore, the step (b) may be performed at 70° C. or more, 75° C. or more, 80° C. or more, or 85° C. or more, 150° C. or less, 140° C. or less, 130° C. or less, 120° C. or less, 110° C. or less, or 100° C. or less. For example, the step (b) may be performed at 90° C., but the present invention is not limited thereto.

Meanwhile, an equivalent ratio of the phenol-based compound and the second acid catalyst may be 1:0.0001 to 0.1. In addition, the first acid catalyst and the second acid catalyst may be the same, and preferably, the same sulfuric acid catalyst may be used to perform the reaction without further adding a catalyst in the step (b).

The total amount of the heat-resistant styrene-based compound reacting in the step (a) may be 0.1 to 3 equivalents with respect to 1 equivalent of the phenol, and the amount of the styrene compound added in the step (b) may be 0.3 to 1 equivalent based on 1 equivalent of the phenol-based compound.

When the amount of the styrene compound added in the step (b) is less than 0.3 equivalent, a final product is solidified, and thus compatibility for application as a non-reactive thinner may be degraded, and when the amount thereof is greater than 1 equivalent, the content of styrenated phenol increases, and thus physical properties of a final product may be changed, and a curing agent part may be discolored when the product is mixed with an epoxy curing part (e.g., Jeffamine D-230), or paint compatibility may be degraded.

The heat-resistant styrene-based compound may react with the first product. For example, α-methylstyrene may react with cumylphenol to produce dicumylphenol. Specifically, the α-methylstyrene may react with p-cumylphenol to produce 2,4-dicumylphenol and may react with o-cumylphenol to produce 2,6-dicumylphenol.

In addition, the styrene compound may react with an unreacted phenol-based compound included in the first product to produce styrenated phenol. Specifically, for example, the styrenated phenol may be mono-styrenated phenol (2-(1-phenyl-ethyl)phenol, 4-(1-phenyl-ethyl)phenol) in which one molecule of styrene is bonded to one molecule of phenol and di-styrenated phenol (2,4-di-(1- phenyl-ethyl)phenol, 2,6-di-(1-phenyl-ethyl)phenol) in which two molecules of styrene are bonded to one molecule of phenol.

Additionally, the styrene compound may react with cumylphenol and dicumylphenol included in the first product to produce an α-methylstyrenated phenol mixture.

Specifically, the second product may include: a mixture of TMPI and DMP at 2 to 10 wt %; cumylphenol at 10 to 50 wt %; dicumylphenol at 30 to 50 wt %; styrenated phenol at 2 to 10 wt %; and α-methylstyrenated phenol, to which styrene has been bonded, at 2 to 20 wt %.

According to a composition ratio of the second product, the additive composition exhibits a difference in viscosity, crystallization, discoloration when mixed with an epoxy curing part, and the like, which leads to a difference in physical properties of the paint.

When the contents of the cumylphenol and the dicumylphenol are within the above-described ranges, adhesive strength can be enhanced during the curing of epoxy paint, and the composition can prevent and delay discoloration when mixed with an epoxy curing part. On the other hand, when the contents thereof are out of the above-described ranges, the composition is solidified, and thus plasticity and compatibility for application as a thinner are degraded.

When the contents of the mono-styrenated phenol (MPS) and the di-styrenated phenol are within the above-described ranges, the plasticity and adhesive strength during the curing of the epoxy paint composition can be enhanced. In addition, plasticity and flexibility among epoxy curing properties can be enhanced. On the other hand, when the contents thereof are out of the above-described ranges, discoloration is caused in mixing with a curing agent part, and thus application of the composition in the field of epoxy coating for varnish may be difficult.

The second product may be subjected to a neutralization reaction with an aqueous basic solution, and the resulting solution may be concentrated under reduced pressure to remove moisture and residual compounds and filtered using a filter to remove salts resulting from the neutralization, finally obtaining a purified additive composition.

The aqueous basic solution may be one selected from the group consisting of an aqueous sodium carbonate solution, an aqueous potassium carbonate solution, an aqueous sodium hydroxide solution, an aqueous potassium hydroxide solution, and a mixture of two or more thereof, but the present invention is not limited thereto. Any aqueous basic solution may be used as long as it can be used to perform the neutralization reaction under mild conditions.

Therefore, when mixed with epoxy paint, the additive composition may be used as a substitute for a conventional alkylphenol thinner composition such as a nonylphenol or a dodecylphenol. Particularly, when mixed with an epoxy curing part, the additive composition has an advantage in which it does not cause or delays discoloration, and thus it can be applied in the varnish field, and paint compatibility can also be enhanced.

The mixture provided in the present invention may be used in both the main material part and curing agent part of epoxy paint, and a mixing ratio of the main material part and the curing agent part may be 1 wt % or more, 5 wt % or more, 10 wt % or more, 15 wt % or more, or 20 wt % or more, 50 wt % or less, 45 wt % or less, 40 wt % or less, 35 wt % or less, or 30 wt % or less in consideration of physical properties of the product.

Hereinafter, exemplary embodiments of the present invention will be described in more detail. However, hereinafter, only experimental results obtained from a few selected exemplary embodiments of the invention will be described, and the scope and contents of the invention should not be interpreted as being reduced or limited by the few selected exemplary embodiments. The effects of each of the various embodiments of the invention which are not explicitly set forth below will be described in detail in relevant sections.

EXAMPLE

A sulfuric acid catalyst (0.135 g, 0.0013 eq) was added to phenol (100 g, 1 eq), and α-methylstyrene (138 g, 1.1 eq) was added dropwise for 120 minutes until the reaction temperature increased to 90° C. from 70° C. After the dropping of α-methylstyrene was completed, the reaction was continued at the same temperature for an hour. The gas chromatography (GC) analysis result of the obtained product showed that a mixture of trimethyl phenyl indane (TMPI) and diphenyl methyl pentene (DMP), cumylphenol, and dicumylphenol were produced in a ratio of 5.06%, 63.28%, and 25.4%, respectively.

Subsequently, styrene (66.4 g, 0.6 eq) was further added dropwise at the same temperature for 60 minutes. After the dropping of styrene was completed, the reaction was continued at the same temperature for an hour to obtain an α-methylstyrenated phenol mixture solution. The obtained solution was neutralized for 60 minutes while adding sodium bicarbonate (0.116 g, 0.0013 eq) having been dissolved in distilled water to the solution at 80° C. The resulting solution was concentrated under reduced pressure to remove moisture and residual compounds and then filtered using a filter to remove salts resulting from the neutralization, thereby obtaining a purified α-methylstyrenated phenol composition. The GC analysis result of the obtained composition showed that a mixture of TMPI and DMP, cumylphenol, dicumylphenol, styrenated phenol, and α-methylstyrenated phenol to which styrene had been bonded were produced in a ratio of 3.35%, 24.47%, 47.89%, 4.42%, and 12.3%, respectively.

Comparative Example 1

A sulfuric acid catalyst (0.250 g, 0.0024 eq) was added to phenol (100 g, 1 eq), and α-methylstyrene (175.8 g, 1.4 eq) was added dropwise at 70° C. for 120 minutes, and as a result, the reaction temperature increased to 90° C. After the dropping of α-methylstyrene was completed, the reaction was continued at the same temperature for an hour, and neutralization was then performed for 60 minutes while adding sodium bicarbonate (0.214 g, 0.0024 eq) having been dissolved in distilled water at 80° C. The resulting solution was concentrated under reduced pressure to remove moisture and residual compounds and then filtered using a filter to remove salts resulting from the neutralization, thereby obtaining a purified α-methylstyrenated phenol composition. The GC analysis result of the obtained composition showed that phenol, a mixture of TMPI and DMP, cumylphenol, and dicumylphenol were produced in a ratio of 2.10%, 4.02%, 49.59%, and 36.72%, respectively.

Comparative Example 2

A sulfuric acid catalyst (0.188 g, 0.0018 eq) was added to phenol (100 g, 1 eq), and α-methylstyrene (276.3 g, 2.2 eq) was added dropwise at 130° C. for 120 minutes, and as a result, the reaction temperature increased to 140° C. After the dropping of α-methylstyrene was completed, the reaction was continued at the same temperature for an hour, and neutralization was then performed for 60 minutes while adding sodium bicarbonate (0.161 g, 0.0018 eq) having been dissolved in distilled water at 80° C. The resulting solution was concentrated under reduced pressure to remove moisture and residual compounds and then filtered using a filter to remove salts resulting from the neutralization, thereby obtaining a purified α-methylstyrenated phenol composition. The GC analysis result of the obtained composition showed that a mixture of TMPI and DMP, cumylphenol, and dicumylphenol were produced in a ratio of 6.85%, 20.38%, and 49.17%, respectively.

Comparative Example 3

Phenol (300 g, 1 eq) and a phosphoric acid ($H_3PO_4$) catalyst (1.876 g, 0.006 eq) were put into a reaction vessel and heated at 140° C., and styrene (381.6 g, 1.15 eq) was then added dropwise thereto for 120 minutes. As the styrene was added dropwise, the reaction temperature increased to 170° C. from 140° C. After the dropping of styrene, the reaction was continued at the same temperature for an hour. In order to remove unreacted materials, the reaction temperature was lowered to 110° C., and a sulfuric acid ($H_2SO_4$) catalyst (0.05 g, 2 to 10 wt % based on the phosphoric acid catalyst) was added to a reaction product. As the sulfuric acid was added, the reaction temperature increased to 125° C., and the reaction was continued for 30 minutes. The temperature of a reaction product was cooled to 80° C., and the reaction product was neutralized for 30 minutes while adding an amount of an aqueous sodium carbonate solution equivalent to that of the sulfuric acid catalyst. The resulting product was concentrated under reduced pressure and filtered using a filter to remove salts resulting from the neutralization, thereby obtaining a styrenated phenol composition. The GC analysis result of the obtained composition showed that the content of mono-styrenated phenol (MSP) was 67 wt % based on the total weight of styrenated phenol.

Experimental Example 1

The compositions produced according to Example and Comparative Examples 1 to 3 were analyzed, and results thereof are shown in the following Table 1.

TABLE 1

| Classification | OH value | Viscosity (cps at 25° C.) | Type | Occurrence of discoloration when mixed with curing agent (D-230) in 1:1 wt % |
|---|---|---|---|---|
| Example | 184 | 3667 | Liquid | X |
| Comparative Example 1 | 201 | 2225 | Crystal | X |
| Comparative Example 2 | 140 | 2800 | Liquid | X |
| Comparative Example 3 | 258 | 500 | Liquid | ○ |

Preparation Examples and Comparative Preparation Examples

A thinner for an epoxy resin requires discoloration prevention and durability, and a dodecylphenol was conventionally used as a thinner or modifier for an epoxy resin. An epoxy paint composition is two-component paint composed of a main material part and a curing agent part, and, in this preparation example, an additive was applied to a main material part.

In order to comparatively analyze the α-methylstyrenated phenol composition produced according to Example with a nonylphenol and a dodecylphenol conventionally used as a thinner for an epoxy resin, a main material part was prepared. KER-828 commercially available from Kumho P&B Chemicals was used as an epoxy resin, and a specific blending ratio is shown in the following Table 2.

TABLE 2

| Classification | Preparation Example 1 | Comparative Preparation Example 1 | Comparative Preparation Example 2 |
|---|---|---|---|
| Epoxy resin | 47.57% | 47.57% | 47.57% |
| Thinner | Example, 5% | Dodecylphenol, 5% | Nonylphenol, 5% |
| Benzyl alcohol | 4.7% | 4.7% | 4.7% |
| Silicon dioxide | 28.5% | 28.5% | 28.5% |
| Titanium dioxide | 14.2% | 14.2% | 14.2% |
| Carbon black | 0.03% | 0.03% | 0.03% |

(Units: wt %)

A blending ratio of a curing agent part to be mixed with the main material part is shown in the following Table 3.

TABLE 3

| Classification | Content |
|---|---|
| Jeffamine D-230 | 95% |
| DMP-30 | 5% |

(Units: wt %)

Jeffamine D-230 is the polyetheramine curing agent commercially available from Huntsman International LLC.

The main material part and the curing agent part were mixed in a weight ratio of 100 (main material part):16.89 (curing agent part) to prepare an epoxy paint composition.

Additionally, for storability evaluation, a thinner and a curing agent were mixed in a weight ratio of 1:1 to prepare an epoxy paint composition, and a blending ratio is shown in the following Table 4.

TABLE 4

| Classification | Preparation Example 2 | Comparative Preparation Example 3 | Comparative Preparation Example 4 |
|---|---|---|---|
| Thinner | Example 50 g | Dodecylphenol 50 g | Nonylphenol 50 g |
| Curing agent | Jeffamine D-230 50 g | Jeffamine D-230 50 g | Jeffamine D-230 50 g |

The curing agent is the most commonly used among curing agents for epoxy resin-based paint for flooring materials. The compositions of Preparation Example 2 and Comparative Preparation Examples 3 and 4 were prepared by sufficiently stirring using a stirrer at 25° C. for 30 minutes.

Experimental Example 2: Measurement of Drying Time of Epoxy Paint Composition

The epoxy paint compositions of Preparation Example 1 and Comparative Preparation Examples 1 and 2 were dried by a crosslinking reaction between an epoxy resin contained in the main material part and an amine contained in the curing agent part when the main material part and the curing agent part were mixed.

A drying time of the epoxy paint composition was evaluated using the BK-drying time recorder commercially available from Elcometer Ltd., and results thereof are shown in the following Table 5. In the evaluation, the time taken until a coating film with a thickness of 400 μm was dried at 25° C. was measured.

TABLE 5

| Classification | Preparation Example 1 | Comparative Preparation Example 1 | Comparative Preparation Example 2 |
| --- | --- | --- | --- |
| Dry to touch | 7.5 hours | 7.5 hours | 7 hours |
| Dry hard | 12.5 hours | 14.5 hours | 12 hours |

Referring to Table 5, it can be seen that the hard drying of Comparative Preparation Example 1 using a dodecylphenol conventionally used as a thinner took the longest time, whereas the hard drying time of Preparation Example 1 using α-styrenated phenol as a thinner and the hard drying time of Comparative Preparation Example 2 using a nonylphenol as a thinner were shortened about 14 to 17% compared to Comparative Preparation Example 1.

Experimental Example 3: Measurement of Pot Life and Reaction Rate of Epoxy Paint Composition The "pot life" means the time in which the epoxy paint composition may be used as paint based on the mixing point of time, and is defined as the amount of time it takes for an initial mixed viscosity to double in accordance with ASTM D-2471.

The reaction rate was calculated from the graph recorded every 20 minutes based on the mixing point of time by measuring the change in viscosity. The slope of the graph is proportional to a reaction rate, and the faster the reaction rate, the larger the slope value.

The viscosity was measured using the Cone&Plate viscometer commercially available from Sheen at 25° C., and results thereof are shown in the following Table 6 and FIG. 2.

TABLE 6

| Classification | Preparation Example 1 | Comparative Preparation Example 1 | Comparative Preparation Example 2 |
| --- | --- | --- | --- |
| Pot life | 35 minutes | 30 minutes | 28 minutes |

Referring to Table 6, it can be seen that the pot life of the epoxy paint composition of Preparation Example 1 using the α-styrenated phenol of Example was increased by about 20% compared to Comparative Preparation Examples 1 and 2 respectively using a dodecylphenol and a nonylphenol conventionally used as thinners.

Figure 2:
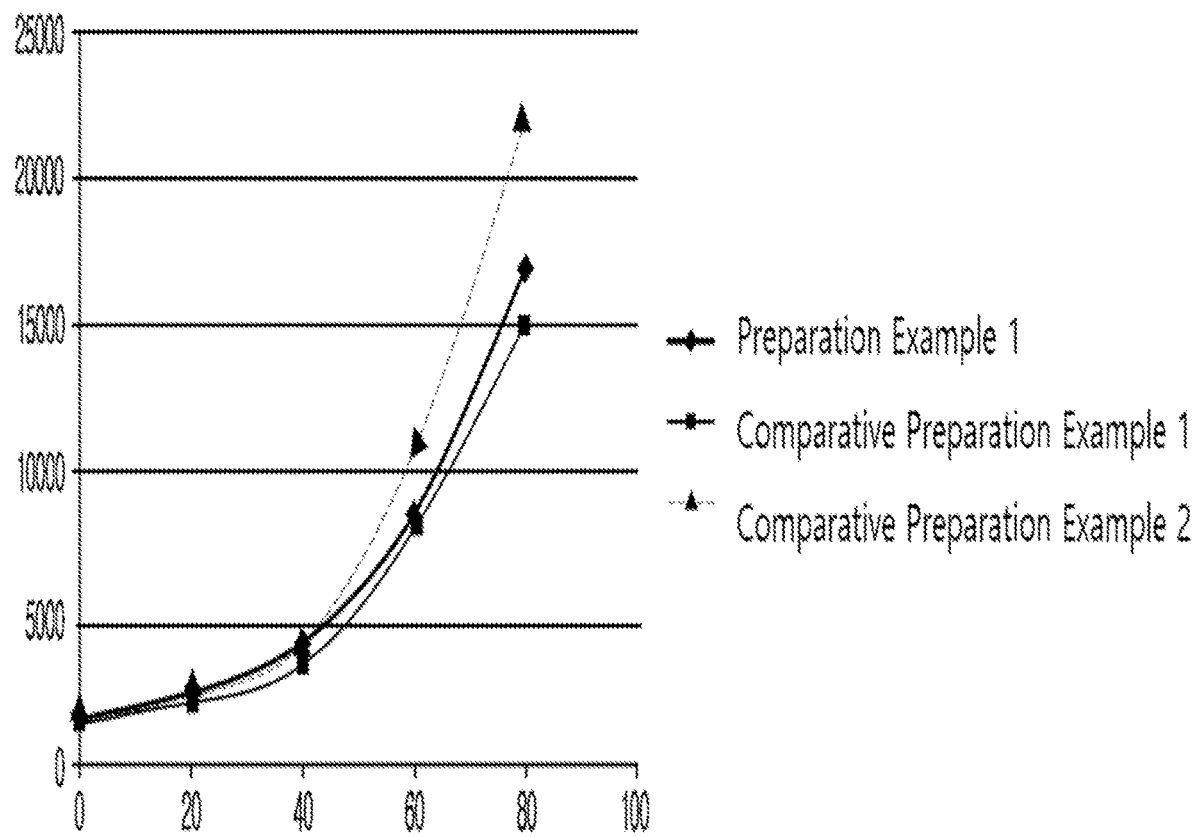
FIG. 2 shows a measurement result of the pot life of an epoxy paint composition including an additive composition according to the example of the present invention.

In FIG. 2, a horizontal axis represents time (units: min) and a vertical axis represents viscosity (units: centipoise). Referring to FIG. 2, the initial viscosity change slopes (reaction rate) were similar, but a difference in slope occurred after 40 minutes. Comparative Preparation Example 2 exhibited the largest slope, and Preparation Example 1 and Comparative Preparation Example 1 exhibited similar slopes.

Experimental Example 4: Evaluation of Abrasion Resistance of Epoxy Paint Composition Abrasion resistance is an important mechanical property in the application of the epoxy paint composition to flooring, which is one of the measures of durability. In order to measure abrasion resistance, a frictional environment was artificially created on the sufficiently cured paint to measure the abrasion resistance of the paint in accordance with ASTM D4060 (Standard Test Method for Abrasion Resistance of Organic Coatings by the Taber Abraser). Before the test, the prepared specimen was cured at 25° C. for a week, and the initial weight thereof was then measured using a precision balance that enables measurement until 0.1 mg and recorded. After the test was completed, the specimen was weighted using the same balance, and a decrement in weight was then recorded. The test was performed by applying two weights of 500 g and then rotating a CS-17 wheel 1000 cycles using the Taber abrasion tester commercially available from Taber Industries at 25° C., and evaluation results thereof are shown in the following Table 7.

TABLE 7

| Classification | Preparation Example 1 | Comparative Preparation Example 1 | Comparative Preparation Example 2 |
| --- | --- | --- | --- |
| Decrement in weight | 70 mg | 96 mg | 95 mg |

Referring to Table 7, it can be seen that Comparative Preparation Examples 1 and 2 exhibited a decrement in weight of 96 mg and 95 mg respectively, whereas Preparation Example 1 exhibited the lowest decrement in weight of 70 mg, which indicates that Preparation Example 1 has superior abrasion resistance.

Experimental Example 5: Evaluation of Weather Resistance of Epoxy Paint Composition The change in paint gloss was measured while artificially applying ultraviolet rays to the epoxy paint composition to evaluate weather resistance. In this test, the QUV equipment commercially available from Q-LAB was used, and the Tri-angle gloss meter commercially available from Elcometer Limited was also used as gloss measurement equipment. Before the test, the prepared specimen was cured at 25° C. for a week, and the initial gloss thereof was then measured and recorded. After the specimen was put into the test equipment, while QUV-A was applied, a change in gloss was recorded at an interval of 10 hours for a total of 40 hours, and results thereof are shown in the following Table 8.

TABLE 8

| Classification | Preparation Example 1 | Comparative Preparation Example 1 | Comparative Preparation Example 2 |
| --- | --- | --- | --- |
| Initial gloss | 98 | 94 | 95 |
| 10 hours | 85.9 | 82.6 | 82.3 |
| 20 hours | 73.2 | 69.1 | 67.6 |
| 30 hours | 57.6 | 48.6 | 47.1 |
| 40 hours | 39.2 | 24.4 | 23.8 |
| Decrement in gloss | 60% | 74% | 75% |

Referring to Table 8, it can be seen that Preparation Example 1 exhibited the highest initial gloss, whereas Comparative Preparation Examples 1 and 2 exhibited a relatively low initial gloss. In addition, it can be seen that Preparation Example 1 exhibited the lowest decrement in gloss of 60% as measured after 40 hours, whereas Comparative Preparation Examples 1 and 2 exhibited a high decrement in gloss of 74% or more, which indicates that Preparation Example 1 has superior weather resistance.

Experimental Example 6: Evaluation of Adhesion of Epoxy Paint Composition

Adhesion is the most basic property in all paints, and is a standard for the protection performance of the object to be coated and the mechanical properties of the paint itself. The cured paint is attached to the object to be coated through a physicochemical bond, and adhesion is determined by adhesion between the object to be coated and the cured paint and cohesion of the cured paint itself.

The adhesion was evaluated in accordance with ASTM D4541 (Standard Test Method for Pull-Off Strength of Coatings Using Portable Adhesion Testers). Carbon steel with a length, width, and thickness of 100 mm, 100 mm, and 2 mm was washed with a solvent, then pre-treated with sandpaper 600 times, and coated with paint with a thickness of 2 mm to prepare a specimen. The specimen was cured at 25° C. for a week and then attached to the dolly of the Elcometer 108 hydraulic adhesion tester commercially available from Elcometer Limited using the Loctite 401 adhesive commercially available from Henkel Corporation. At least 4 hours after the attachment, the specimen was detached, and adhesive strength and peeling patterns were recorded. The test was performed two times in the same manner, and test results are shown in the following Table 9.

TABLE 9

| Round | Classification | Preparation Example 1 | Comparative Preparation Example 1 | Comparative Preparation Example 2 |
| --- | --- | --- | --- | --- |
| 1st | Adhesive strength | 12 MPa | 10 MPa | 13 MPa |
| | Peeling pattern | 100% Glue failure | 40% Adhesion failure 60% Glue failure | 20% Adhesion failure 80% Glue failure |
| 2nd | Adhesive strength | 12 MPa | 10 MPa | 12.5 MPa |
| | Peeling pattern | 100% Glue failure | 40% Adhesion failure 60% Glue failure | 80% Adhesion failure 20% Glue failure |

Referring to Table 9, it can be seen that both of Comparative Preparation Examples 1 and 2 exhibited interfacial failure (adhesion failure) which represents the peeling between the surface of the object to be coated and the cured paint, whereas Preparation Example 1 exhibited no adhesion failure, which indicates that Preparation Example 1 has superior adhesion.

Comparative Preparation Example 1 exhibited an adhesive strength of 10 MPa, whereas Preparation Example 1 and Comparative Preparation Example 2 exhibited excellent adhesive strengths of 12 MPa and 13 MPa, respectively.

Experimental Example 7: Evaluation of Storability of Epoxy Paint Composition A common phenol-based derivative thinner is structurally modified when reacted with an amine-based compound used as a curing agent for epoxy paint, and as a result, red or yellow discoloration occurs. In order to evaluate whether or not the α-styrenated phenol prepared in the present invention was discolored, a thinner and a curing agent were mixed to prepare epoxy paint compositions of Preparation Example 2 and Comparative Preparation Examples 3 and 4.

A Gardner color was measured and recorded immediately after the preparation of epoxy paint compositions of Preparation Example 2 and Comparative Preparation Examples 3 and 4. Afterward, the composition was placed in an airtight glass container and stored in a 50° C. oven, and a Gardner color was then measured and recorded at an interval of 2 days. The Gardner color was measured using OME-2000 commercially available from Nippon Denshoku Industries Co., Ltd., and test results are shown in the following Table 10 and FIG. 3.

TABLE 10

| Classification | Initial color (G) | Color after 2 weeks (G) |
| --- | --- | --- |
| Preparation Example 2 | 0.3 | 0.5 |
| Comparative Preparation Example 3 | 0.7 | 2.0 |
| Comparative Preparation Example 4 | 0.6 | 2.0 |

Figure 3:
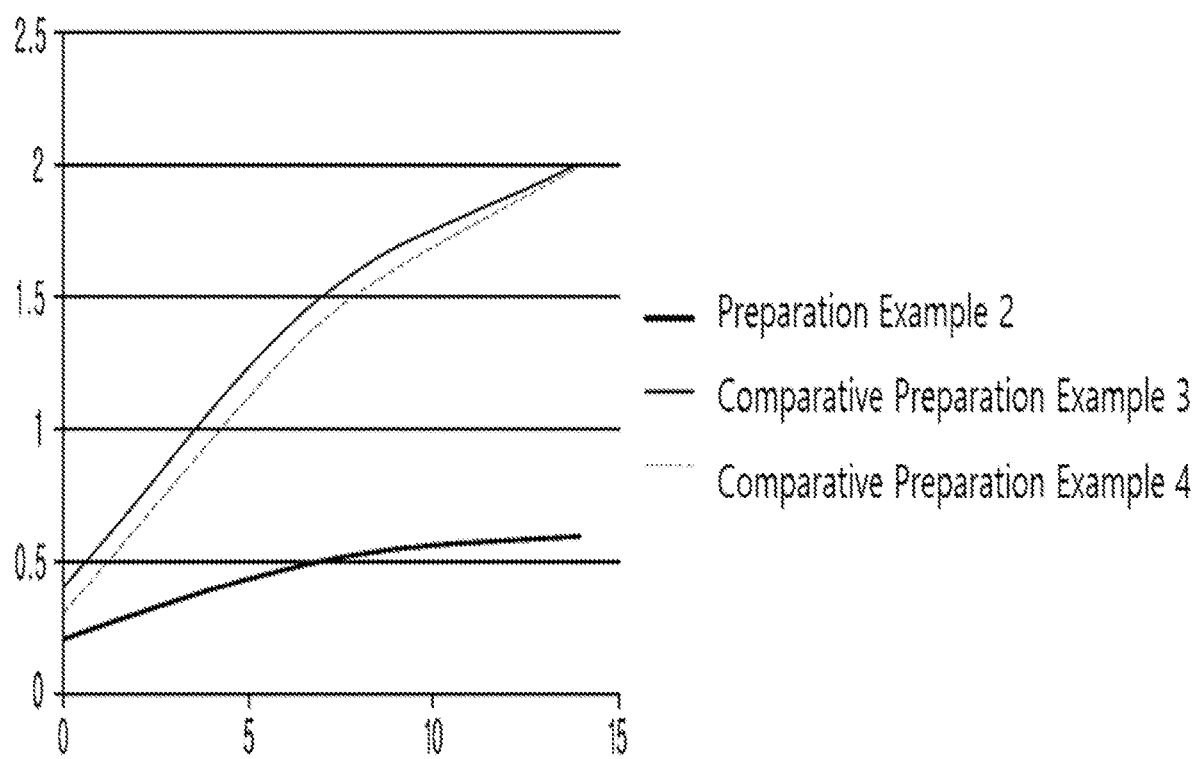
FIG. 3 shows a measurement result of the Gardner color variation of an epoxy paint composition including an additive composition according to the example of the present invention.

In FIG. 3, a horizontal axis represents time (units: day) and a vertical axis represents the Gardner index. Referring to Table 10 and FIG. 3, it can be seen that Comparative Preparation Examples 3 and 4 exhibited the discoloration pattern of a common phenol-based derivative thinner, whereas Preparation Example 2 exhibited the lowest discoloration degree, which indicates that Preparation Example 2 has superior storage stability.

After the mixture of a thinner and a curing agent was stored at room temperature for 2 weeks, it can be visually confirmed that the color of Comparative Preparation Examples 3 and 4 turned yellow compared with the initial color, whereas in the case of Preparation Example 2, it was difficult to visually determine a color difference from the initial color.

As described above, it can be seen that the α-methylstyrenated phenol composition prepared according to Example can enhance compatibility and plasticity when mixed with a main material part and curing agent part for epoxy paint, and can also enhance storage stability compared to Comparative Examples 1 to 3 or substances conventionally used as a non-reactive thinner such as nonylphenols, dodecylphenols, and the like.

According to one aspect of the present invention, an additive composition which can be mixed with both a main material part and curing agent part for paint while maintaining a drying time or compatibility at the level of a conventional thinner including a nonylphenol or a dodecylphenol and suppresses a discoloration issue that occurs when mixing with a curing agent for paint, and a method of preparing the same can be provided.

According to another aspect of the present invention, when the additive composition is prepared, the process stages are subdivided, and the amounts of reactants and catalysts used in each stage are adjusted to keep the composition of the product including α-methylstyrenated phenol constant, thereby reproducibility and reliability can be enhanced.

In addition, when applied as an additive for epoxy paint and the like, the additive composition according to one aspect of the present invention can exhibit excellent compatibility and excellent plasticity and can enhance the curing properties of the paint, such as discoloration prevention, durability, scratch resistance, adhesive strength, and the like.

However, it is to be understood that the effects of the present invention are not limited to the above-described effects but include all effects deducible from the configuration of the invention described in the detailed description of the invention or in the claims.

The foregoing description of the present invention is intended for illustration, and it will be understood by those skilled in the art to which the invention pertains that the invention can be easily modified and implemented in various other forms without changing the technical spirit or essential features of the invention. Therefore, it should be understood that the embodiments described above are only exemplary in all aspects and not limiting. For example, each of the constituents described as being one combined entity may be implemented separately, and similarly, constituents described as being separate entities may be implemented in a combined form.

It should be understood that the scope of the present invention is defined by the following claims and that all changes or modifications derived from the meaning and scope of the claims and their equivalents are included in the scope of the invention.

What is claimed is:

1. An additive composition comprising:
    a first compound, which is produced by reacting a phenol-based compound and a heat-resistant styrene-based compound, at 40 to 100 parts by weight;
    a second compound, which is produced by reacting the phenol-based compound and styrene, at 2 to 10 parts by weight;
    a third compound, which is produced by reacting the phenol-based compound, the heat-resistant styrene-based compound, and styrene, at 2 to 20 parts by weight; and
    a mixture of trimethyl phenyl indane and diphenyl methyl pentene at 2 to 10 parts by weight,
    wherein the heat-resistant styrene-based compound is one selected from the group consisting of α-methylstyrene, α-ethylstyrene, methyl-α-methylstyrene, and a mixture of two or more thereof.

2. The additive composition of claim 1, wherein the first compound comprises a compound in which a reaction ratio of the phenol-based compound and the heat-resistant styrene-based compound is 1:1 and a compound in which the reaction ratio thereof is 1:2 in a weight ratio of 1:2 to 4.

3. A mixture of the additive composition of claim 1 and an amine based compound, wherein the mixture when stored under a condition of 50° C., has a Gardner color variation of 0.5 G/week or less.

4. An epoxy paint composition comprising:
    an epoxy resin or an epoxy curing agent; and
    the additive composition of claim 1.

5. The epoxy paint composition of claim 4, wherein the epoxy paint composition has a pot life of 30 minutes or more.

6. A method of preparing an additive composition, comprising:
    (a) preparing a first product by reacting, in the presence of a first acid catalyst, a phenol-based compound and a heat-resistant styrene-based compound; and
    (b) preparing a second product by further reacting, in the presence of a second acid catalyst, the first product with 0.3 to 1 equivalent of styrene based on 1 equivalent of the phenol-based compound,
    wherein the heat-resistant styrene-based compound is one selected from the group consisting of α-methylstyrene, α-ethylstyrene, methyl-α-methylstyrene, and a mixture of two or more thereof.

7. The method of claim 6, wherein the first acid catalyst and the second acid catalyst are each one selected from the group consisting of sulfuric acid, p-toluenesulfonic acid, methanesulfonic acid, phosphoric acid, a boron trifluoride complex, clay, an ion exchange resin, and a mixture of two or more thereof.

8. The method of claim 7, wherein the first acid catalyst and the second acid catalyst are the same.

9. The method of claim 6, wherein an equivalent ratio of the phenol-based compound and the first acid catalyst is 1:0.0001 to 1.

10. The method of claim 6, wherein the heat-resistant styrene-based compound is reacted in an amount of 0.1 to 3 equivalents based on 1 equivalent of the phenol-based compound.

11. The method of claim 6, wherein the first product comprises:
    a mixture of trimethyl phenyl indane and diphenyl methyl pentene at 1 to 10 wt %;
    cumylphenol at 30 to 70 wt %;
    dicumylphenol at 10 to 40 wt %; and
    phenol as the remainder.

12. The method of claim 6, wherein the second product comprises:
    a mixture of trimethyl phenyl indane and diphenyl methyl pentene at 2 to 10 wt %;
    cumylphenol at 10 to 50 wt %;
    dicumylphenol at 30 to 50 wt %;
    styrenated phenol at 2 to 10 wt %; and
    α-methylstyrenated phenol, to which styrene has been bonded, at 2 to 20 wt %.

* * * * *